US008637248B2

(12) United States Patent
Takahama et al.

(10) Patent No.: US 8,637,248 B2
(45) Date of Patent: Jan. 28, 2014

(54) METHOD OF DETERMINING THE HAPLOTYPE OF MULTIPLE ALLELIC GENES

(75) Inventors: Shin-ichiro Takahama, Matsudo (JP); Yuri Mizutani, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 390 days.

(21) Appl. No.: 12/516,521

(22) PCT Filed: Nov. 30, 2007

(86) PCT No.: PCT/JP2007/073621
§ 371 (c)(1),
(2), (4) Date: May 27, 2009

(87) PCT Pub. No.: WO2008/069288
PCT Pub. Date: Jun. 12, 2008

(65) Prior Publication Data
US 2010/0075318 A1    Mar. 25, 2010

(30) Foreign Application Priority Data

Dec. 1, 2006  (JP) .................................. 2006-325951

(51) Int. Cl.
*C12Q 1/68* (2006.01)
*C12P 19/34* (2006.01)
(52) U.S. Cl.
USPC ......................................... 435/6.12; 435/91.2
(58) Field of Classification Search
None
See application file for complete search history.

(56) References Cited

U.S. PATENT DOCUMENTS

| 6,476,215 | B1 | 11/2002 | Okamoto et al. | |
|---|---|---|---|---|
| 2004/0229224 | A1* | 11/2004 | Frazer et al. ...................... | 435/6 |
| 2005/0089877 | A1* | 4/2005 | Shim et al. ......................... | 435/6 |
| 2005/0260607 | A1 | 11/2005 | Kao et al. | |
| 2007/0003958 | A1 | 1/2007 | Okamoto et al. | |
| 2007/0122848 | A1 | 5/2007 | Mizutani | |
| 2007/0122899 | A1 | 5/2007 | Mizutani | |
| 2007/0184457 | A1* | 8/2007 | Pont-Kingdon et al. .......... | 435/6 |

FOREIGN PATENT DOCUMENTS

| EP | 0 237 362 A1 | 9/1987 |
|---|---|---|
| EP | 1 178 119 A2 | 2/2002 |
| JP | 62-214355 A | 9/1987 |
| JP | 11-187900 A | 7/1999 |
| JP | 2002-272482 A | 9/2002 |
| WO | 93/18177 A1 | 9/1993 |
| WO | 03/018835 A2 | 3/2003 |

OTHER PUBLICATIONS

Latorra et al., Enhanced Allele-Specific PCR Discrimination in SNP Genotyping Using 30 Locked Nucleic Acid (LNA) Primers, Human Mutation 22:79-85 (2003).*
Pawlikowska et al., A mouse genetic model for familial cholestasis caused by ATP8B1 mutations reveals perturbed bile salt homeostasis but no impairment in bile secretion,Human Molecular Genetics, 2004, vol. 13, No. 8 881-892.*
Luther et al., Overlapping Roles of CXCL13, Interleukin 7 Receptor and CCR7 Ligands in Lymph Node Development,Chemokine and Cytokine Requirements for Lymph Node Development, vol. 197, No. 9, May 5, 2003, pp. 1191-1198.*
PCT International Search Report and Written Opinion of the International Searching Authority in International Application No. PCT/JP2007/073621, Mailing Date Mar. 4, 2008.
Search Report dated Nov. 22, 2010 in European Application No. 07850229.1.
Michalatos-Beloin, et al., "Molecular haplotyping of genetic markers 10 kb apart by allele-specific long-range PCR", Nucleic Acids Research, vol. 24, No. 23, 1996, pp. 4865-4867.
Official Action dated Feb. 21, 2011 in Canadian Application No. 2,671,210.
Official Action dated Aug. 9, 2011 in European Application No. 07 850 229.1.
Indian Office Action dated Feb. 21, 2013 in Indian Application No. 3843/CHENP/2009.
Michalatos-Beloin, et al., "Molecular haplotyping of genetic markers 10 kb apart by allele-specific long-range PCR", Nucleic Acids Research, vol. 24, No. 23, 1996, pp. 4841-4843.
Australian Office Action dated Sep. 3, 2012 in Australian Application No. 2007329856.
European Office Action dated Aug. 8, 2013 in European Application No. 07850229.1.
Zhang, et al., "Single-base mutational analysis of cancer and genetic diseases using membrane bound modified oligonucleotides", Nucleic Acids Research, vol. 19, No. 14, 1991, pp. 3929-3933.
Cronin, et al., "Cystic Fibrosis Mutation Detection by Hybridization to Light-Generated DNA Probe Arrays", Human Mutation, vol. 7, 1996, pp. 244-255.

* cited by examiner

*Primary Examiner* — Kenneth R. Horlick
*Assistant Examiner* — David Thomas
(74) *Attorney, Agent, or Firm* — Fitzpatrick, Cella, Harper & Scinto (57) ABSTRACT

In amplifying a region containing two allelic genes, the polymorphism of one of the allelic genes is positioned at or near the 3' end of an amplification primer, so that the chain would extend only from one of the two primers, one that matches the mutant type nucleotide(s) and one that matches the wild-type nucleotide(s). The other primer is unaffected by the allelic genes but is positioned to include the other allelic gene in the amplicon. The PCR amplifies only the target genomic DNA having one specific allele of the first allelic gene. The technique exploits the fact that the haplotype of the first and the second allelic genes can be determined if the allele of the second allelic gene in the amplicon can be identified. Designing probes with complementary sequences for identifying the two alleles (major and minor) of the second allelic gene, and fixing the probe set on a solid support and hybridizing them with the amplicon to identify the probe that forms a hybrid, are characteristic features of the present invention.

2 Claims, 4 Drawing Sheets

| 94°C | 1min. |
| 94°C | 60sec. |
| 66.5°C | 30sec. |
| 68°C | 5min. |
| 68°C | 7min. |
| 15°C | ∞ |

35 CYCLES

FIG. 4

| 95°C | 5min. |
| 95°C | 30sec. |
| 60°C | 30sec. |
| 72°C | 30sec. |
| 10°C | ∞ |

35 CYCLES

FIG. 5

SEQUENCE LISTING

```
<160> NUMBER OF SEQ ID NOS: 7

<210> SEQ ID NO 1
<211> LENGTH: 15
<212> TYPE: DNA
<213> ORGANISM: Artificial
<220> FEATURE:
<223> OTHER INFORMATION: Primer

<400> SEQUENCE: 1
agggcggcag aggtc                                                     15

<210> SEQ ID NO 2
<211> LENGTH: 19
<212> TYPE: DNA
<213> ORGANISM: Artificial
<220> FEATURE:
<223> OTHER INFORMATION: Primer
```

```
<400> SEQUENCE: 2
ctactcttcc ttggcctttt                                              19

<210> SEQ ID NO 3
<211> LENGTH: 176
<212> TYPE: DNA
<213> ORGANISM: Homo sapiens

<400> SEQUENCE: 3
agggcggcag aggtcctgag gctccctac cagaagcaaa catggatggt gggtgaaacc    60
acaggctgga ccagaagcca ggctgagaag gggaagcagg tttgggggac ttcctggaga   120
agggcattta tacatggcat gaaggactgg attttccaaa ggccaaggaa gagtag       176

<210> SEQ ID NO 4
<211> LENGTH: 22
<212> TYPE: DNA
<213> ORGANISM: Artificial
<220> FEATURE:
<223> OTHER INFORMATION: Probe

<400> SEQUENCE: 4
tctccaggac gtcccccaaa cc                                            22

<210> SEQ ID NO 5
<211> LENGTH: 22
<212> TYPE: DNA
<213> ORGANISM: Artificial
<220> FEATURE:
<223> OTHER INFORMATION: Probe

<400> SEQUENCE: 5
tctccaggaa gtcccccaaa cc                                            22

<210> SEQ ID NO 6
<211> LENGTH: 27
<212> TYPE: DNA
<213> ORGANISM: Artificial
<220> FEATURE:
<223> OTHER INFORMATION: Primer

<400> SEQUENCE: 6
gttatcccag aaggctttgc aggcttc                                       27

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
gccgactgag ccctgggagg taggta                                        26
```

METHOD OF DETERMINING THE HAPLOTYPE OF MULTIPLE ALLELIC GENES

TECHNICAL FIELD

The present invention relates to a method of determining the haplotype of a target nucleic acid having at least two heterozygous polymorphisms, and the primer set used for such determination.

BACKGROUND ART

A haplotype is the cis arrangement of two or more polymorphisms located on a single chromosome. Haplotype information is considered to be very useful because the haplotype is related to certain diseases or abnormalities, and specific drug sensitivities. Until now, haplotype analysis required tracking studies of genetic information about polymorphisms covering several generations of a family, and computing machine-based estimation algorithms. On the other hand, the advances in polymerization chain reaction (PCR) technology have enabled direct, molecular level analysis of DNA, and the use of the results of such analysis for determining the haplotype has been suggested. However, for determining the haplotype using PCR, it is necessary to use multiple combinations of primers specific to the allelic genes, and to carry out PCR a number of times. If we consider only 2 allelic genes, there have been attempts to determine the haplotype by positioning 2 primer pairs at the polymorphic sites and examining whether any amplification occurred. This method has been suggested for determination of the haplotype with a single test tube assay (see Japanese Patent Application Laid-Open No. 2002-272482). To be more specific, a forward primer containing the first polymorphism is modified with a label that yields different signals depending on the allele type on the 5' end. Moreover, for the reverse primer containing the second polymorphism, a flap sequence that is not present in the target sequence is attached to the 5' end, so that the primer is designed to yield an amplicon having a length that depends on the allele. Using these primers, allele-specific PCR assay is carried out from both the directions. Which primer pair caused amplification, can be known by detecting the fluorescent label in the PCR amplicon and from the length of the amplicon, and thus the haplotype can be determined.

In the above described known method, however, it is essential that the primers contain sites with the polymorphic sequences. This restricts the freedom of selecting the base sequence of the primers. Here, to carry out allele-specific PCR, the $T_m$s of the primers used for the PCR have to be similar. However, with the above described restrictions in selecting the primer base sequences, it may be difficult in some cases to make the $T_m$s of the primers similar. In other words, with the method of the Japanese Patent Application Laid-Open No. 2002-272482, highly accurate detection of the haplotype is likely to be restricted to cases where the polymorphisms are at locations for which primers of similar $T_m$ can be used. Besides this, in this method of detection, it is difficult to shift the positions of the sequences of both the forward and reverse primers. Thus, if the forward and reverse primers form a primer dimer, it becomes impossible to detect the haplotype.

DISCLOSURE OF THE INVENTION

The present invention provides a method of haplotype determination with better accuracy irrespective of the location of the polymorphisms. More specifically, the invention provides a method of determining the haplotype of the target nucleic acid having at least two heterozygous polymorphisms, and the primer set used for this purpose.

The method of the present invention determines the haplotype of a target nucleic acid having a first heterozygous polymorphic site on the 3' side and a second heterozygous polymorphic site on the 5' side, and the method is characterized by including (i) carrying out PCR of the target nucleic acid using one of the forward primers (a-1), i.e., (a-1-1) a forward primer that contains a base sequence complementary to the first polymorphic site and can extend the target nucleic acid if the first polymorphism is the mutant type, and does not extend the target nucleic acid if the first polymorphism is the wild type, and (a-1-2) a forward primer that contains a base sequence complementary to the first polymorphic site and can extend the target nucleic acid if the first polymorphism is the wild type, and does not extend the target nucleic acid if this first polymorphism is the mutant type, and (b-1) a reverse primer that contains a base sequence complimentary to a certain base sequence that does not contain the second polymorphism, and is located on the 3' side of the second polymorphism, on the complimentary strand of the target nucleic acid; and (ii) hybridizing the product obtained as a result of (i) with a first probe that has a base sequence identical with a certain segment of the base sequence of the target nucleic acid, which contains the wild-type nucleotide of the second polymorphism, and a second probe that has a base sequence identical with a certain segment of the base sequence of the target nucleic acid, which contains the mutant nucleotide of the second polymorphism, and detecting the signals of hybrid formation with the first and second probes.

The primer set used for determining the haplotype according to the present invention is a primer set for determining the haplotype of a target nucleic acid having the first polymorphic site on the 3' side and the second polymorphic site on the 5' side, and the primer set is characterized by having one of a forward primers i.e., a forward primer that contains a base sequence complementary to the first polymorphic site and can extend the target nucleic acid if the first polymorphism of the target nucleic acid is the mutant type, and does not extend the target nucleic acid if the first polymorphism of the target nucleic acid is the wild type, and a forward primer that contains a base sequence complementary to the first polymorphic site and can extend the target nucleic acid if the first polymorphism of the target nucleic acid is the wild type and does not extend if the first polymorphism is the mutant type, and a reverse primer that contains a base sequence complimentary to a certain base sequence that does not contain the second polymorphism, and is located on the 3' side of the second polymorphism, on the complimentary strand of the target nucleic acid.

As described above, the present invention can simultaneously and exhaustively determine the haplotype when multiple heterozygous polymorphisms are present.

BEST MODES FOR CARRYING OUT THE INVENTION

In the present invention, an allelic gene-specific PCR amplification protocol is used for the polymorphisms of interest in the genomic DNA targeted for determining the haplotype with a microarray. Firstly, an amplicon that is specific to one of the alleles of the first allelic gene, and also contains the second allelic gene, is produced. This amplicon is then hybridized with oligonucleotide probes, each specific to one of the alleles of the second allelic gene, to identify the allele of the second allelic gene. This technique can be a very powerful method of detection at the molecular level when the first and second allelic genes form a haplotype. A complementary strand probe that forms a DNA hybrid when the second allelic gene is the major allele, and another complimentary strand probe that forms a DNA hybrid if the second allelic gene is the minor allele, are prepared and fixed on a solid support, such as a microarray. The haplotype can be determined by verifying, with a label, the probe with which hybridization occurs. When there are multiple pairs of allelic gene candidates, the N haplotypes can be analyzed exhaustively by hybridizing with N×2 probes loaded on a solid support. If the first allelic gene is a pre-selected heterozygous one, exclusive solid supports can be prepared for identifying the haplotypes. One of the amplification primers can be designed in such a way that it becomes specific to one of the alleles of one allelic gene, and another amplification primer must be designed to include the other allelic genes in the amplicon. The label can, for instance, be a fluorophore carried on the primer and structured in such a way that the fluorescence can be detected in the probe hybridized with the other allelic gene only when allele-specific amplification has occurred successfully.

One of the forward primers described below is used in the present invention to obtain an amplicon having the region specific to one of the alleles of the first allelic gene.

(a-1-1) A forward primer that contains a base sequence complementary to the above described first polymorphic site and can extend the target nucleic acid if the first polymorphism of the target nucleic acid is the mutant type, and does not extend if the first polymorphism is the wild type.

(a-1-2) A forward primer that contains a base sequence complementary to the above described first polymorphic site and can extend the target nucleic acid if the first polymorphism of the target nucleic acid is the wild type, and does not extend if the first polymorphism is the mutant type.

In these forward primers, the base sequence of the primer (and/or the length of the sequence) can be set by a standard method on the basis of the sequence of a segment containing the known first polymorphism, based on typing of the target nucleic acid, in such a manner that this segment would be obtained in the PCR amplicon.

Either the mutant type or the wild-type polymorphism can be selected.

The reverse primer for obtaining, in the amplicon, the segment containing the second polymorphism is designed to have a base sequence complementary to a certain base sequence that does not contain the second polymorphism, from the 3' side of the second polymorphism on the complementary strand of the target nucleic acid. The base sequence (sequence length) of the reverse primer can be set by a standard method, using as basis, the sequence of the segment containing the known second polymorphism, based on typing of the target nucleic acid, and in such a way that this segment can be obtained in the PCR amplicon.

With the probes used for detecting the segment containing the second polymorphism also, a sequence specific to this segment can be selected and the base sequence (and/or the sequence length) of the probe that can detect the selected sequence can be set by the standard method, as the segment containing the second polymorphism is already known from typing of the target nucleic acid.

The embodiments of the present invention are described below.

First Embodiment

The first embodiment of this invention is described below referring to FIG. 1. This embodiment concerns the technique of determining the allele types of multiple allelic genes on the genomic DNA. More specifically, the procedure of determining the haplotype of 2 or more than 2 allelic genes is described below sequentially.

In this embodiment, the haplotypes of two heterozygous allelic genes on the genomic DNA are determined. The distance between the two allelic genes may range from about a few base pairs to a few tens of base pairs to as much as a few hundred to a few thousand base pairs. Therefore, it is necessary to prepare an amplicon having both the allelic genes. The two allelic genes are defined here as the first allelic gene and the second allelic gene, counting from the 5' side. The major allele of the first allelic gene is G and the minor allele is C, and the major allele of the second allelic gene is G and the minor allele is T.

For determining the haplotype in this embodiment, a primer's 3' end is matched to the locus of the allele to selectively amplify either the major or the minor allele of the first allelic gene. For example, the first primer (the forward primer) is designed to be complementary to the minor allele of the first allelic gene at its 3' end so that extension would occur if the first allelic gene is the minor allele and extension would not proceed if it were the major allele. On the other hand, the second primer (reverse primer) of the opposite strand is designed to interpose the second allelic gene using the binding position of the first primer as the reference point. The second primer does not depend on the allele type. With this arrangement, if the first allelic gene is the minor allele, a large amount of amplicon is produced, which confirms that the first allelic gene is the minor allele, and the amplicon containing the second allelic gene has been preferentially produced. Therefore, by determining the allele type of the second allelic gene in the amplicon, we can determine the haplotype of the first and the second allelic genes.

The method of determining the haplotype according to the present invention includes the steps 1) and 2) described below:

1) selecting one of the alleles of the first allelic gene, and producing the amplicon containing the second allelic gene only;

2) hybridizing the amplicon with complementary probes specific to the alleles for the second allelic gene, and thereby identifying the allele of the second allelic gene.

Figure 1:
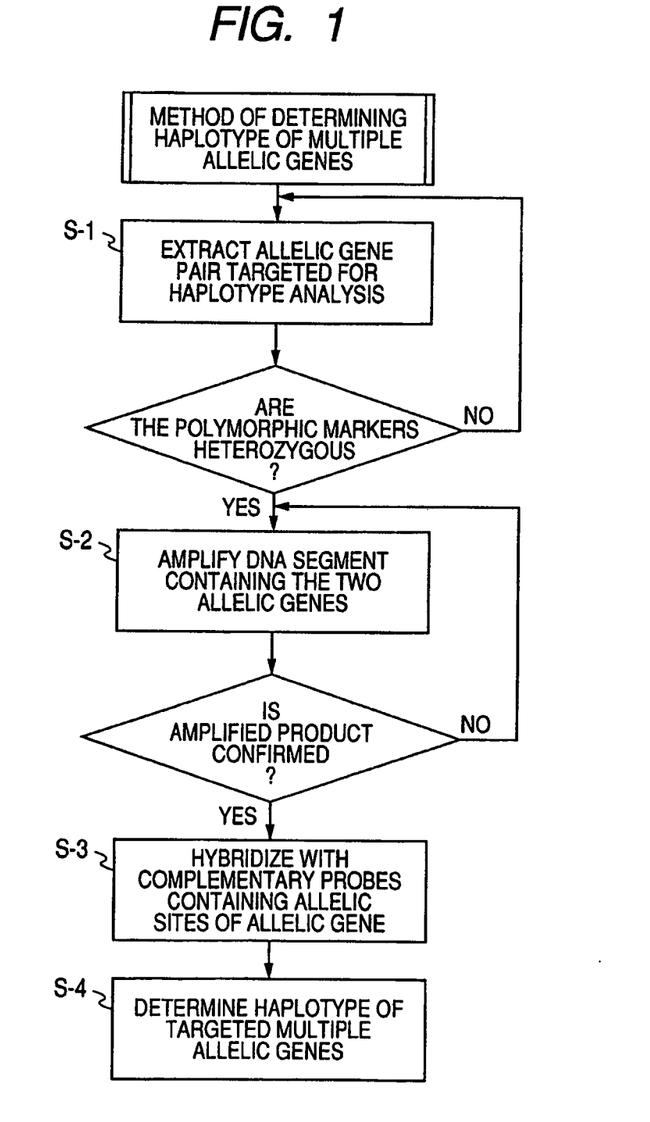
FIG. 1 is a flowchart of the determination of haplotypes of two allelic genes in the first embodiment of the present invention.

FIG. 1 is a flowchart illustrating the above described steps. S-1 is a step to confirm that both the first and second allelic genes are heterozygous. There is no restriction on the method of typing used for each allelic gene. If at least one out of the first and second allelic genes is homozygous, the haplotype combination of the two allelic genes becomes known, and there is no need to apply the present invention.

Only the combinations where the heterozygosity has been confirmed after each genotyping are targeted in this embodiment. S-2 is the step in which the amplicon is obtained from the target genome through the combined use of a first primer specific to, the minor allele of the first allelic gene and a second primer of the opposite strand for including the second allelic gene. The first primer specific to the minor allele of the first allelic gene is a primer in which the mutant site is positioned at its 3' end so that it is complementary, and the primer does not get extended if the target genomic sequence has the major allele. Here, as the first allelic gene is heterozygous, the extension reaction advances only when the genome of the minor allele and the first primer get annealed. In other words, the amplicon formed would be limited to one having the minor allele of the first allelic gene. The second primer is not influenced by the target genome, and will produce an amplicon containing the second allelic gene matching its configuration in the target genome. In this case, where the first allelic gene is the minor allele, an amplicon containing the matching allele of the second allelic gene is formed. Whether the second allelic gene is the major or minor allele does not have any effect, but the haplotype with the first allelic gene can be determined by hybridizing the amplicon with probes specific to the alleles of the second allelic gene. The essence of the present invention remains the same even when the first primer is designed to be specific to the major allele, unlike in the above described case.

A label also needs to be used for determining the second allelic gene. Either the first or the second primer can be labeled. Alternatively, a labeled nucleotide is incorporated into the amplicon in the course of the extension reaction. The label can be a fluorophore, a chemiluminescent substance, or a radioisotope. A Cy3 fluorescent dye label is used in this embodiment. S-3 is a step where the amplicon is allowed to hybridize with the solid support on which probes specific to the second allelic gene have been fixed. Probes, each specific to the major or the minor allele, are prepared. These probes can be fixed on a solid support or used in an arrangement that would cause FRET in a liquid phase reaction. In this embodiment, the second allelic gene is determined using the solid support. In other words, if fluorescence is seen only at the particular location on the solid support where the probe specific for the minor allele of the second allelic gene is positioned, this means that the first and second allelic genes form a minor/minor haplotype. At the same time, this also confirms the existence of the major/major haplotype. On the other hand, if fluorescence is seen only at the particular location on the solid support where the probe specific for the major allele of the second allelic gene is positioned, this means that the first and second allelic genes form a minor/major haplotype, which simultaneously confirms the existence of the major/minor haplotype. Moreover, if fluorescence is seen at both the sites on the solid support, where the two probes, one specific to the major allele and the other to the minor allele of the second allelic gene, are positioned, it should be interpreted that the first and second allelic genes have weak haplotype association. Thus, S-4 is the step where the alleles of the second allelic gene and the haplotype of the first and second allelic genes are determined.

Figure 2:
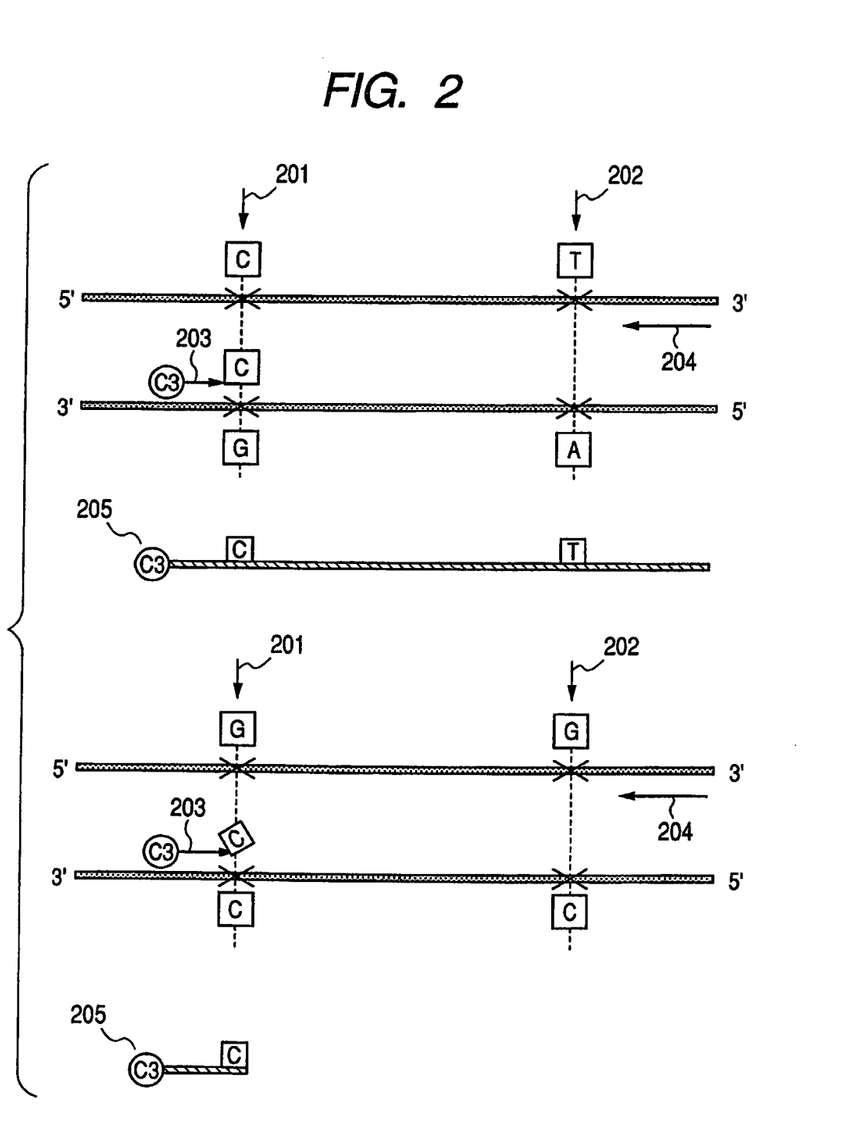
FIG. 2 is a diagram that illustrates the arrangement of the two allelic genes in the first embodiment of the present invention.

FIG. 2 is a diagram illustrating the positional relationship of the above described first allelic gene 201 and the second allelic gene 202 on the target genome. The first primer 203 and the second primer 204 and their amplicon 205 are also illustrated in the diagram. As described earlier, the 3' end of the first primer 203 corresponds to the mutant site of the first allelic gene 201, and the second primer 204 is positioned downstream of the region that contains the second allelic gene 202. Because of the first primer 203, the production of the extension product, which contains one of the alleles of the first allelic gene 201 (upper part of the FIG.), is greater than the production of the extension product containing the other allele (lower part of the FIG.). In other words, the PCR amplifies only that side of the target genome that contains one of the two alleles of the first allelic gene 201. Therefore, the second allelic gene 202 will also have the allele matching only that side of the target genome. Besides this, the probes are designed to contain the alleles of the second allelic gene 202 shown in the diagram.

Table 1 shows the base sequences of a pair of amplification primers, their amplicon, and the probes for the second allelic gene, all pertaining to this embodiment. Starting from the 5' side, the bold characters correspond to the allelic locus (mutant nucleotide C) of the first allelic gene, and the allelic locus (mutant nucleotide T) of the second allelic gene, in that order. The mutant nucleotide C has been selected for the forward primer (FP).

TABLE 1

| | |
|---|---|
| Forward primer (FP) | 5'-AGGGCGGCAGAGGTC-3'<br>(SEQ ID NO. 1) |
| Reverse primer (RP) | 5'-CTACTCTTCCTTGGCCTTT-3'<br>(SEQ ID NO. 2) |
| Amplicon | 5'-AGGGCGGCAGAGGTCCTGAGGCTCCCCT<br>ACCAGAAGCAAACATGGATGGTGGGTGAAAC<br>CACAGGCTGGACCAGAAGCCAGGCTGAGAAG<br>GGGAAGCAGGTTTGGGGGACTTCCTGGAGAA<br>GGGCATTTATACATGGCATGAAGGACTGGAT<br>TTTCCAAAGGCCAAGGAAGAGTAG-3'<br>(SEQ ID NO. 3) |
| Probe for the major allele G of the second allelic gene | 5'-TCTCCAGGACGTCCCCCAAACC-3'<br>(SEQ ID NO. 4) |
| Probe for the minor allele T of the second allelic gene | 5'-TCTCCAGGAAGTCCCCCAAACC-3'<br>(SEQ ID NO. 5) |

Second Embodiment

Figure 5:
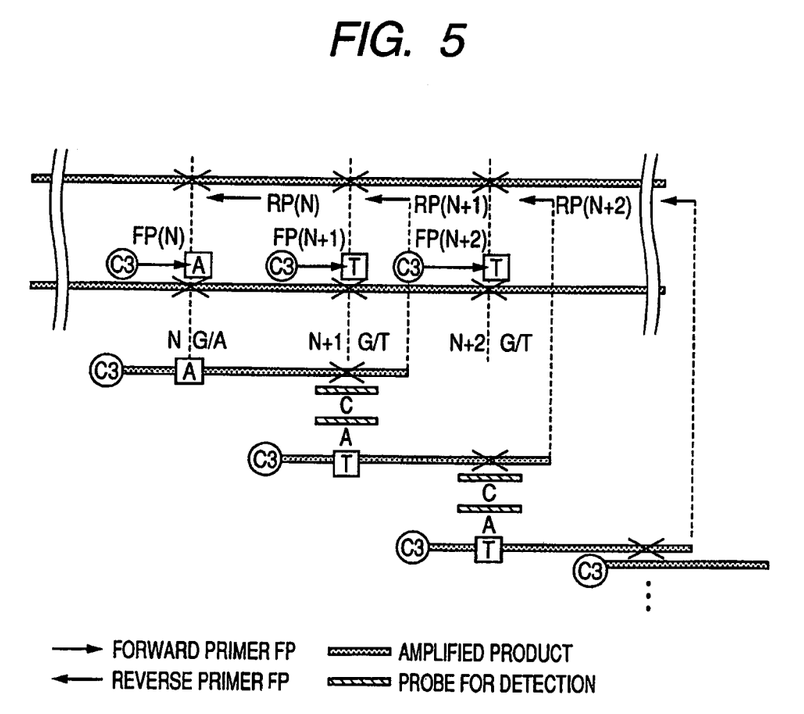
FIG. 5 is a diagram that illustrates the arrangement of two or more multiple allelic genes in the second embodiment of the invention.

The second embodiment of the invention is described below, referring to FIG. 5. The polymorphic locus of each allelic gene is marked with "x". Only the polymorphisms at the loci N, N+1, and N+2 are illustrated here. Others are omitted, which does not imply any limits on the number of polymorphisms. In this case, the forward primer is Cy3-labeled, but the essential features of the invention would of course not change even when it is the reverse primer or the extending nucleotide chain itself that is labeled.

For this embodiment, we shall describe a generalized technique for determining the haplotype of multiple allelic genes. N number of heterozygous polymorphisms are tested here. As can be seen in FIG. 5, FP(N) (the forward primer for the Nth polymorphism) and RP(N) (the reverse primer for the opposite direction) are defined. For N+1 onwards also, we can similarly define the forward primers FP (N+1), FP(N+2), . . . , and the reverse primers RP(N+1), RP(N+2), . . . . The forward primer FP(N) and the reverse primer RP(N+1) are designed to produce the PCR amplicon containing the Nth polymorphism and the N+1th polymorphism. FP(N) is designed to have, at its 3' end, the Nth polymorphism, with one of the two alleles selected. RP(N+1) is designed on the opposite side of the Nth polymorphism in such a way that the PCR amplicon would contain the N+1th polymorphism. The primer pair of FP(N) and RP(N+1) is the pair that would yield a PCR amplicon containing the Nth polymorphism and the N+1th polymorphism when the Nth polymorphism matches with only one of the two alleles. Reaction products are then obtained from m number of PCR amplifications, for N=1, 2, 3, . . . , m, and hybridized with probes that can determine the N+1th allelic gene for the Nth allelic gene selected by FP(N). In the case described here, the probes designed to match the 2×m alleles are fixed at the desired positions on the microarray.

The amplicons obtained in the m PCR amplifications are mixed and hybridized with the probes on the microarray according the protocol described for the following Example 1. By doing this, the haplotype combinations of multiple allelic genes can be determined exhaustively with a single labeling. Moreover, the technique of this invention, i.e., identifying the allele by finding out which of the two probes, with sequences corresponding the two alleles of one allelic gene, undergoes hybridization, improves the accuracy of analyzing the haplotype.

Here we have limited the discussion to heterozygous allelic genes. Two sets of primers individually specific to two alleles of the first allelic gene can be prepared and hybridization carried out separately, for the determination.

EXAMPLES

Example 1

An example according to the first embodiment is described below.

I. Specimen Preparation and Extraction of a Specific Region of the Genome

The template DNA used was prepared by amplifying only a 5 kbp region of the metabolic enzyme gene CYP2D6 of the genomic DNA extracted from a B cell line derived from a Japanese individual, and diluting the amplicon to 8 ng/µL with ultra pure water. This processing was done to eliminate duplicated sequence regions, such as CYP2D7 and CYP2D8, which are pseudogenes, and to obtain the pure CYP2D6 region. To be more specific, the generally, widely used primers listed in Table 2 were used.

TABLE 2

| 2D6-DPKup | GTTATCCCAGAAGGCTTTGCAGGCTTC (SEQ ID NO. 6) |
|---|---|
| 2D6-DPKlow | GCCGACTGAGCCCTGGGAGGTAGGTA (SEQ ID NO. 7) |

Figure 3:
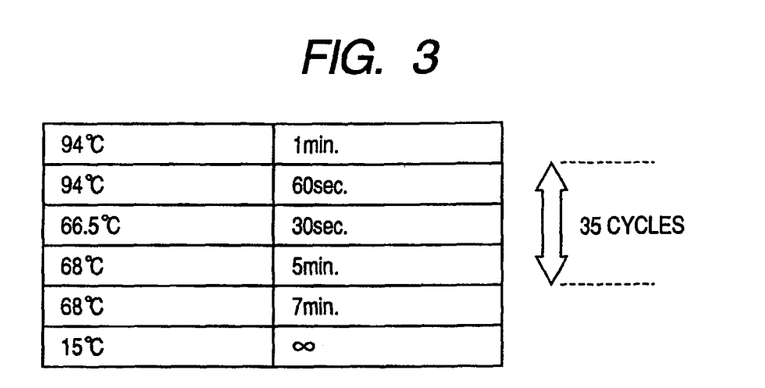
FIG. 3 is a diagram that illustrates the protocol used for the PCR amplification for extracting specific segments of the genome in the first embodiment of the present invention.

The PCR solution was prepared as shown in Table 3 and the PCR cycle was done as described in FIG. 3, and as a result, the amplicon (5079 bp) of the CYP2D6 gene region was obtained.

In the reaction process, the 3-step cycle of denaturation, annealing, and extension was repeated 35 times, and the amplicon was purified by a purification process, after cooling.

The PCR amplicon was purified on a purification column (Qiagen QIAQUICK PCR Purification Kit), and the volume of the PCR amplicon solution was adjusted to 50 µL. A part of the purified PCR amplicon solution thus obtained was sampled and subjected to electrophoresis by a standard method, and it was confirmed from the size of the product that the desired PCR product had been synthesized. The product was further diluted to 8 ng/µL with pure water.

TABLE 3

| Expand Long Enzyme Mix (Roche) | 0.375 µL |
|---|---|
| 2D6-DPKup (1 µM) | 4 µL |
| 2D6-DPKlow (1 µM) | 4 µL |
| Buffer 1 | 2.5 µL |
| dNTP (10 mM each) | 0.875 µL |
| H₂O | 12.25 µL |
| Genome DNA | 1 µL |
| Total | 25 µL |

II. PCR Amplification
Designing the Primers and Purification of the PCR Amplicon Table 4 lists the reagents used in the amplification reaction and their mixing ratio. The concentrations and the amounts used, of the PCR buffer, DNA polymerase, nucleotides, primers and template DNA are also listed here. A Cy3-labelled primer was used here.

TABLE 4

| Item | Concentration | Amount [µl] |
|---|---|---|
| H₂O | — | 17.3 |
| Forward Primer (FP) | 10 µM | 1.0 |
| Reverse Primer (RP) | 10 µM | 1.0 |
| 10 × Buffer | 4 µM | 2.5 |
| dNTP (dATP, dGTP, dCTP, dTTP) | 2 mM for each | 2.5 |
| Ampli Taq Gold (TAKARA) | | |
| Template DNA | 8 ng/µl | 0.2 |
| Total | — | 25.0 |

Figure 4:
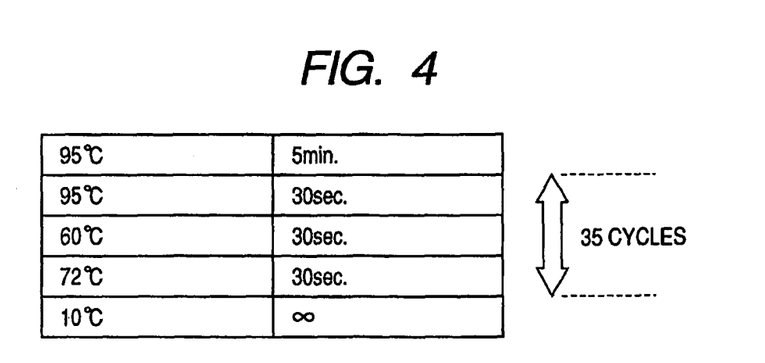
FIG. 4 is a diagram that illustrates the protocol used for the PCR amplification in the first embodiment of the present invention.

FIG. 4 illustrates the protocol applied for the amplification reaction. In the reaction process, the 3-step cycle of denaturation, annealing, and extension was repeated 35 times, and the amplicon was then purified, by a purification process, after cooling.

The PCR amplicon was purified on a purification column (Qiagen QIAQUICK PCR Purification Kit). After the purification, the volume of the PCR amplicon solution was adjusted to 50 µL. A part of the purified PCR amplicon solution thus obtained was sampled and subjected to electrophoresis by a standard method, and it was confirmed from the size of the product that the desired PCR product had been synthesized. The sequences of the primers used and the amplicon were as shown earlier in Table 1.

III. Preparation of the Microarray
(1) Designing the Probes

Two probes were designed for the above described PCR product. As in the designing of the primers, the probes were designed with careful consideration so that each probe can specifically recognize the base sequence of the alleles of the second allelic gene. In this probe design, the DNA strand that extends from the forward primer FP is the one that forms the hybrid with a probe. The base sequence of each probe was designed carefully, by adjusting the base pair length, etc taking the stability of the hybrid formed into account. The sequences of the two designed probes are shown in Table 1.

(2) Synthesis of the Probes and Preparation of the Microarray

Synthesis of the probes and preparation of the microarray were carried out using the methods of preparing DNA microarrays disclosed by Canon Inc. (Japanese Patent Application laid-open No. 11-187900). In short, for processing the substrate, quartz glass was treated with a silane coupling agent, and EMCS bound to it, to introduce maleimide groups on the surface. As for probe synthesis, probes in which a thiol group was introduced at the 5' end were synthesized and purified by HPLC. For preparing the DNA microarray, each probe was spotted on the glass substrate using a modified version of an ink jet printer (proprietary name BJF-850, manufactured by Canon Inc.). The size of the glass substrate was 25 mm×75 mm×1 mm (W×L×T).

IV. Hybridization

Hybridization on microarray was done using the DNA microarray prepared in III and the PCR amplicon prepared in II as the nucleic acid specimen sample.

(1) Blocking the DNA Microarray

BSA (bovine serum albumin Fraction V, manufactured by Sigma Co.) was dissolved in 100 mM NaCl/10 mM phosphate buffer to the concentration 1 wt. %. The DNA microarray prepared in III was immersed in this solution for 2 hours at room temperature to get the glass substrate surface blocked. After the blocking, it was washed with 2×SSC solution (NaCl 300 mM and sodium citrate (trisodium citrate dihydrate, i.e., $C_6H_5Na_3 \cdot 2H_2O$) 30 mM, pH 7.0) containing 0.1 wt. % SDS (sodium dodecyl sulfate). It was then rinsed with pure water. After that the DNA microarray was dried in a spin-drier.

(2) Preparation of Hybridization Solution

The hybridization solution was prepared using 2 μL of the PCR amplicon solution to achieve the final concentration given below. The hybridization solution had the following composition.

6×SSPE/10% formamide/PCR amplicon solution (6×SSPE: NaCl 900 mM, $NaH_2PO_4 \cdot H_2O$ 60 mM, and EDTA 6 mM, pH 7.4)

(3) Hybridization

The dried DNA microarray was set in a hybridization apparatus (Hybridization Station, Genomic Solutions Inc.) and the hybridization reaction carried out using the hybridization solution with the above described composition, following the procedures and conditions given below.

The hybridization conditions and procedures used were as follows:

The hybridization solution was heated to 65° C., maintained at that temperature for 3 minutes, and held at 92° C. for 2 minutes and then at 50° C. for 4 hours. After that, it was washed at 40° C., with 2×SSC containing 0.1% SDS. It was further washed at 25° C., with 2×SSC and rinsed with pure water as needed, following the ordinary manual, and finally dried in a spin-drier.

(4) Fluorescence Measurement

After completing the hybridization reaction, the fluorescence originating from the hybrid was measured on the spin-dried DNA microarray using a DNA microarray fluorescence scanner (Genepix 4000B, manufactured by Axon). The results of measurement obtained for each probe are given below in Table 5.

TABLE 5

| Probe type | Brightness of fluorescence (relative to the value at 535 nm) |
| --- | --- |
| Major allele | 530 |
| Minor allele | 1800 |

In calculating the brightness, the fluorescence intensity on parts of the DNA microarray with no probe DNA spot was taken as the background value; and the apparent fluorescence intensity of each spot minus the background value was taken as the measured fluorescence intensity. The measurements were made twice, and the mean values are given here.

From the results, the haplotype of the first allelic gene and the second allelic gene was determined to be C/T (minor/minor). Also, because both the allelic genes were heterozygous, the diplotype was determined to be G/G (major/major). Here, we have limited ourselves to heterozygous allelic genes. Two sets of primers individually specific to the two alleles of the first allelic gene may also be prepared and hybridization carried out separately.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2006-325951, filed Dec. 1, 2006, which is hereby incorporated by reference herein in its entirety.

The invention claimed is:

1. A method of determining the haplotype of a target nucleic acid having a first heterozygous polymorphic site on the 3' side and a second heterozygous polymorphic site on the 5' side, comprising:
   (i) carrying out PCR of the target nucleic acid using one of the forward primers (a-1) listed below,
      (a-1-1) a forward primer that contains a base sequence complementary to the first polymorphic site and can extend the target nucleic acid if the first polymorphism is the wild type, and does not extend the target nucleic acid if the first polymorphism is the mutant type, and
      (a-1-2) a forward primer that contains a base sequence complementary to the first polymorphic site and can extend the target nucleic acid if the first polymorphism is the wild type, and does not extend the target nucleic acid if the first polymorphism is the mutant type, and
   (b-1) a reverse primer that contains a base sequence complementary to a certain base sequence that does not contain the second polymorphism, and is located on the 3' side of the second polymorphism, on the complementary strand of the target nucleic acid; and (ii) hybridizing the product obtained as a result of (i) with a first probe that has a base sequence identical with a certain segment of the base sequence of the target nucleic acid, which contains the wild-type nucleotide(s) of the second polymorphism, and a second probe that has a base sequence identical with a certain segment of the base sequence of the target nucleic acid, which contains the mutant nucleotide(s) of the second polymorphism, and detecting the signals of hybrid formation with the first and second probes, wherein the hybridization (ii) with the product obtained as a result of (i) comprises hybridizing a probe carrier on which the first probe and the second probe are fixed at respective different locations, and wherein the haplotype is determined irrespective of the locations of the first and second polymorphisms by using only one primer pair, the primer pair consisting of the forward primer (a-1-1) or (a-1-2) and the reverse primer (b-1).

2. The method of determining the haplotype according to claim 1, wherein the forward primer (a-1-1) has, at or near its 3' end, a nucleotide(s) complementary to the first polymorphism having a mutant type nucleotide(s), and the forward primer (a-1-2) has, at or near its 3' end, a nucleotide(s) complementary to the first polymorphism having a wild type nucleotide(s).

* * * * *